United States Patent

Gourley

[11] Patent Number: 5,207,707
[45] Date of Patent: May 4, 1993

[54] TRI-LEAFLET ALL CARBON HEART VALVE

[75] Inventor: Monti R. Gourley, Austin, Tex.
[73] Assignee: Carbomedics, Inc., Austin, Tex.
[21] Appl. No.: 821,973
[22] Filed: Jan. 16, 1992
[51] Int. Cl.[5] .............................................. A61F 2/24
[52] U.S. Cl. ...................................................... 623/2
[58] Field of Search ........................................... 623/2

[56] References Cited

U.S. PATENT DOCUMENTS

| | | | |
|---|---|---|---|
| 3,952,334 | 4/1976 | Bokros et al. | 623/2 X |
| 3,969,130 | 7/1976 | Bokros | 623/2 X |
| 4,406,022 | 9/1983 | Roy | 623/2 |
| 4,451,937 | 6/1984 | Klawitter | 623/2 |
| 4,624,822 | 11/1986 | Arru et al. | 623/2 X |
| 4,778,461 | 10/1988 | Pietsch et al. | 623/2 |
| 4,820,299 | 4/1989 | Philippe et al. | 623/2 |
| 4,888,009 | 12/1989 | Lederman et al. | 623/2 |
| 4,888,010 | 12/1989 | Bokros | 623/2 |
| 5,026,391 | 6/1991 | McQueen et al. | 623/2 |
| 5,061,278 | 10/1991 | Bicer | 623/2 |
| 5,123,918 | 6/1992 | Perrier | 623/2 |

Primary Examiner—Randall L. Green
Assistant Examiner—Elizabeth M. Burke
Attorney, Agent, or Firm—John R. Merkling

[57] ABSTRACT

A tri-leaflet heart valve wherein the leaflets have supporting ears adapted to slide in curved tracks provided in an annular body. The leaflets ears are further supported and guided by conical-segment surfaces adjacent the curved grooves. A common stop between two grooves for adjacent leaflets limits the motion of the leaflets as the valve closes. Posts between opposed grooves for each leaflet arrest the motion of a leaflet if the leaflets are closing simultaneously closed position. Each leaflet comprises a substantially planar surface with a central vertex where all three leaflets meet in closed position. Edges of the leaflets adjacent the curved grooves are canted up-stream and are scalloped to form ears which slide in the curved grooves.

12 Claims, 2 Drawing Sheets

TRI-LEAFLET ALL CARBON HEART VALVE

BACKGROUND OF MY INVENTION

My present invention pertains to heart valve prostheses and in particular, to tri-leaflet mechanical heart valve prostheses having both a surrounding annular body and leaflets comprised principally of pyrolitic carbon.

DESCRIPTION OF RELATED ART

Various types of heart valve prostheses have been proposed, and many give generally satisfactory operation. One popular design for a heart valve prosthesis includes an annular valve body in which a pair opposed leaflet occluders are pivotally mounted. The occluders are movable between a closed, mated position, blocking blood flow in an upstream direction and minimizing regurgitation, and an open position, allowing blood flow in a downstream direction. In a bi-leaflet mechanical heart valve, pivots and ears for the leaflets or occluders are usually located near a diameter of the supporting annular body. Blood flows through the annular body and past the leaflets in either two or three principal areas. Most of the blood flows between the annular body and a leaflet in a generally semicircular area. In addition, some of the blood may pass between the two leaflets, giving a third area of flow. These areas are all substantially smaller than the total interior area of the annular body. Consequently, increased turbulence can be expected as blood flows through these narrowed passageways, with consequent loss of hemodynamic energy.

The natural heart valve is a biologic structure with three leaflets which open from the center to provide a maximum open area for blood flow. Such a structure gas obvious advantages for reducing resistance to flow and for decreasing turbulence. Although well adapted to the tissues of the body, however, such a design is difficult to implement as a mechanical heart valve because the pivot points of each leaflets are not at right angles to the interior walls of the annular body. The pivot points usually comprise a pivot or ear on the leaflet mating with a recess or guide structure on the annular body. To increase reliability, wear characteristics, and responsiveness of the occluders, continued improvement in design is called for.

Moreover, it is important that an implanted heart valve be biocompatible. This criteria places substantial limitations on the materials which may be selected for use in the design. Properties of the selected materials also place substantial limitations on an appropriate design. Although some metals and metal alloys are suitable for long-term implantation, carbon, and in particular pyrolitic carbon, has demonstrated a superior biocompatibility, particularly in contact with blood. This material is hard, relatively brittle, and very wear resistant. A design suitable for implementation as in all carbon structure, cannot have some of the features of a design for a more malleable material.

With the foregoing in mind, it has been a principal object of my invention to provide a tri-leaflet heart valve which can be constructed with an annular body and leaflets comprised principally of pyrolitic carbon.

It has been an object of my own invention to provide an all carbon tri-leaflet heart valve with pivots which maximize response to applied hemodynamic forces.

It has been a further object of my invention to provide a tri-leaflet heart valve with leaflets which open to maximize a central flow area.

These and other objects and features of my invention will be apparent from the following description taken with reference to the accompanying drawings.

SUMMARY OF MY INVENTION

I have invented a tri-leaflet heart valve wherein the leaflets have supporting ears adapted to slide in curved tracks provided in an annular body. The leaflets ears are further supported and guided by surfaces of revolution adjacent the curved grooves. A common stop between two grooves for adjacent leaflets limits the motion of the leaflets as the valve closes. Posts between opposed grooves for each leaflet act as stops if the leaflets do not close simultaneously.

Each leaflet comprises a substantially planar surface with a central vertex where all three leaflets meet in closed position. Edges of the leaflets adjacent the curved grooves are canted up-stream and are scalloped to form ears which slide in the curved grooves.

DETAILED DESCRIPTION OF MY PREFERRED EMBODIMENT

I will now describe my invention by reference to the drawings. Like numerals designate like parts throughout.

Figure 1:
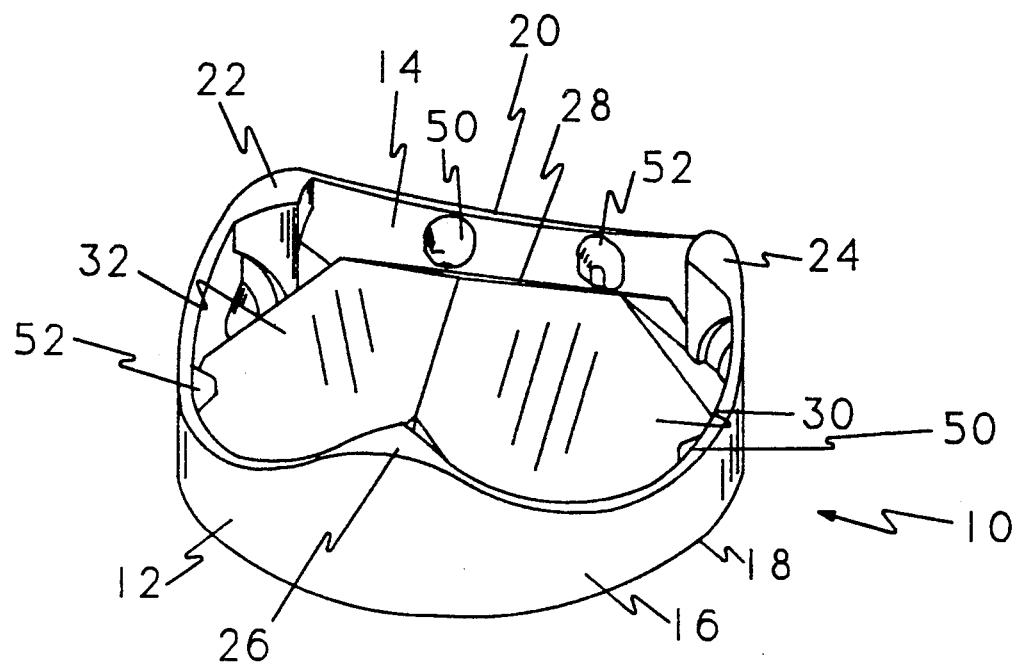
FIG. 1 is a down-stream perspective view of a tri-leaflet heart valve prosthesis according to my present invention, with leaflets closed.

FIG. 1 illustrates a tri-leaflet heart valve prosthesis generally designated 10. The prosthesis 10 comprises an annular valve body 12 which has a generally cylindrical inner surface 14 and an outer surface 16. Mechanical heart valves are attached to the heart with a suture ring. I have not illustrated a suture ring in connection with this description as they are well-known in this art.

An up-stream edge 18 of the annular body is generally planar. A down-stream edge 20, on the other hand, is curved, forming three prominences equidistant from each other around the circumference of the annular body. These prominences are the locations for pivot structures 22, 24, 26 about which leaflets 28, 30, 32 pivot, as will be more fully described below. The structure of each pivot structure is similar and can best be understood with reference to FIGS. 2 and 3.

Each pivot structure, such a pivot structure 26, has inclined walls 34, 36 which meet at a vertex 38. The vertex 38 runs parallel to the axis of the annular body 12. On each face 34, 36 there is a curved groove 40, 42 which supports a portion of a leaflet as more fully described below. The grooves 40, 42 are convex adjacent to the vertex 38 and concave away from the vertex 38. At the concave side of each curved groove 40, 42, there is a curved surface 44, 46 respectively. I will explain the structure of the curved grooves and curved surfaces more particularly below.

A common stop 48 protrudes from the walls 34, 36 of the curved grooves 40, 42 near the up-stream end of the vertex 38.

Figure 4:
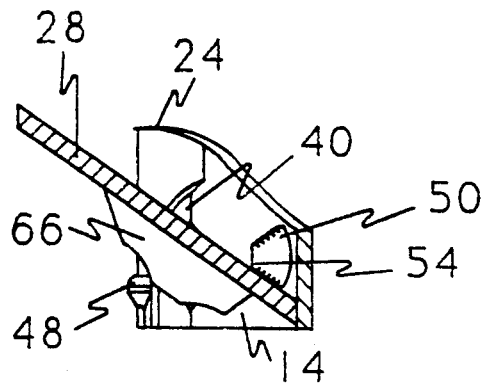
FIG. 4 is the partial sectional view of the heart valve taken along broken line 4—4 of FIG. 2 with the leaflet shown in closed position.

Between each pair of pivot structures, I have provided a pair of posts 50, 52 which stop the leaflets 28, 30, 32 as they close. If the leaflets are not closing simultaneously, the motion of some of the leaflets will be arrested by the posts until all the leaflets are fully closed. Each post is generally trapezoidal in shape with chamfered corners. Fulcrum posts are generally longer in the dimension parallel to the axis of the annular body. An up-stream edge 54 is inclined so that a leaflet can seat against it when closing as seen in FIG. 4.

Figure 2:
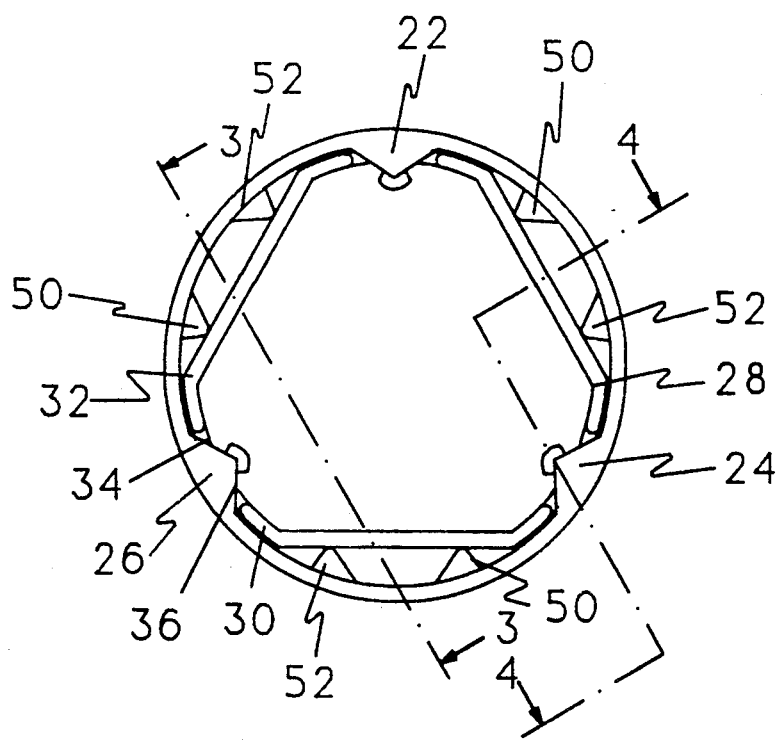
FIG. 2 is a plan view of the heart valve of FIG. 1, viewed from down-stream with leaflets in an open position.
Figure 3:
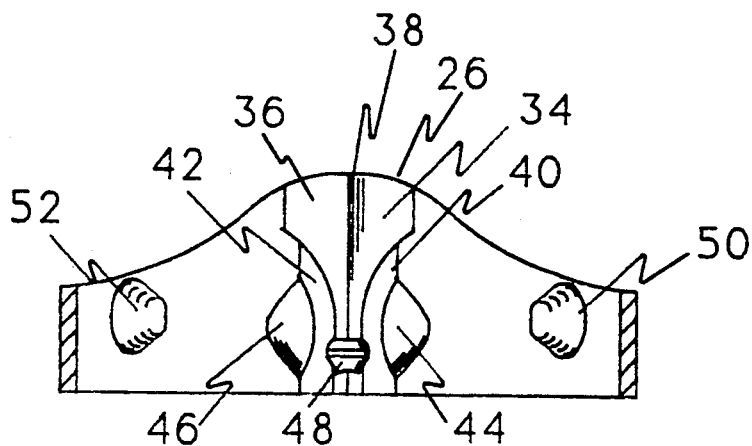
FIG. 3 is a sectional plan view of the heart valve taken along line 3—3 of FIG. 2, with the leaflets omitted.
Figure 5:
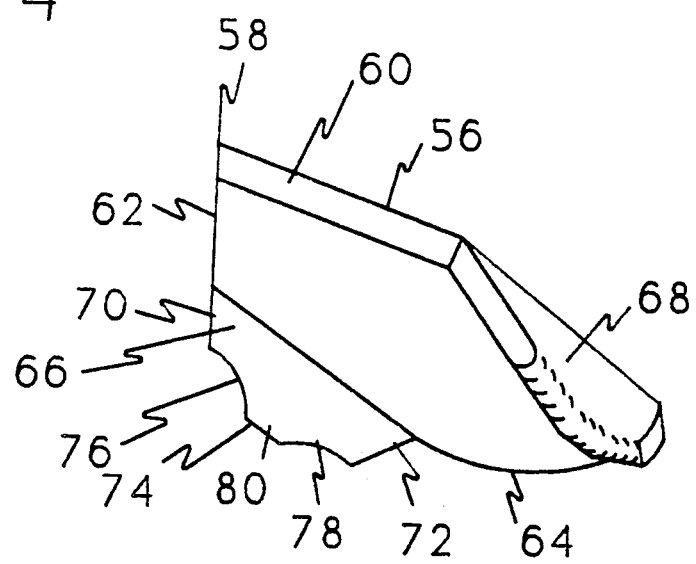
FIG. 5 is an up-stream perspective view of a leaflet.

Each of the leaflets 28, 30, 32 is similar, and I will describe them by reference to the leaflet 28 shown in perspective view in FIG. 5. The leaflet 28 comprises a planar central surface 56 having a central vertex 58 where all three leaflets meet in closed position. From the vertex 58, two central edges 60, 62 diverge at a mating angle slightly less than 120°. The actual mating angle will be determined by the angle chosen for the closing position of the leaflet, as shown if FIG. 4. Adjacent the inner surface 14 of the annular body 12, the valve 28 has a curved mating edge 64. Because the leaflets are not perpendicular to the walls of the annular body when closed, the edge 64 is ellipsoid, rather than circular. Between the edges 60, 62 and the curved edge 64 there are canted surfaces 66, 68. The canted surfaces 66, 68 are bent up-stream from the plane of the planar surface 56. The canted edges are generally trapezoidal in shape with an inner edge 70 and an outer edge 72 tapering toward each other from the planar surface 56. The inner edge 70 and the outer edge 72 are joined by a pivot edge 74 which is scalloped with an inner arc 76 and an outer arc 78 to form a central ear 80. The ear slides in the curved groove 40 as the leaflet 28 pivots between open and closed positions. The outer arc 78 slides along the curved surface 44. In closed position, the curved edge 64 of the leaflet rests against the inner surface 14 of the annular body 12, as seen in FIG. 4. The ear 74 is stopped by the common stop 48. In open position, the ear 74 slides in the curved groove 40 while the leaflet pivots around the posts until the canted edges 68, 70 rest against the inner surface 14, as seen in FIG. 2.

To accommodate this action, curved groove 40 and curved surface 44 form a surface of revolution. If an axis is constructed through a bottom corner 54 the post, such as post 50 shown in FIG. 4, and a similar bottom corner of its adjacent post, such as post 52 (see FIG. 2.), a surface of revolution can be constructed using the inner and outer arcs 76, 78 and central ear 80 of a leaflet. The curved groove and curved surface are formed as a surface of revolution about this axis, which a cord of the annular valve body 12.

The structure which I have described can be formed in pyrolitic carbon with both an all-carbon leaflets and an all-carbon annular body. Of particular importance is the provision of the curved surfaces which retain the leaflets in position and within their required path without a prominence or protrusion.

My invention may be embodied in other specific forms without departing from the spirit or essential characteristics thereof. My invention therefore, is defined by the appended claims, and not by the foregoing description, and all embodiments which come with the meaning of equivalency of the claims are meant to be encompassed therein.

I claim as my invention:

1. A tri-leaflet prosthetic heart valve comprising
   an annular body having an inner surface and being disposed around a central axis; and
   three substantially identical leaflets mounted in said annular body and configured to translate between a closed position impeding blood flow through the valve and an open position permitting blood flow through the valve;
   said annular body having three symmetrically placed pivot structures spaced around an inner surface of said annular body for pivotally supporting said leaflets, each pivot structure having a plane of symmetry containing said central axis and having curved grooves placed on opposing sides of said plane of symmetry, each groove having a convex edge adjacent said plane of symmetry, a concave edge spaced away from said convex edge, and a curved surface segment adjacent said concave edge; and
   each of said leaflets having opposed ears for slidingly engaging said curved grooves and a concave edge adjacent each of said ears for slidingly engaging said curved surface segment.

2. The tri-leaflet prosthetic heart valve according to claim 1 wherein the annular body and the leaflets are composed substantially of a non-metallic substance.

3. The tri-leaflet prosthetic heart valve according to claim 2 wherein the non-metallic substance is substantially pyrolitic carbon.

4. The tri-leaflet prosthetic heart valve according to claim 1 wherein each of said leaflets further comprises
   a central planar surface having a curved outer edge for engaging the inner surface of said annular body and an obliquely angled inner edge for engaging adjacent leaflets; and
   two canted substantially planar outer surfaces, each outer surface supporting one of said ears and concave edges, said outer surfaces being deflected from said planar surface towards an upstream side of said valve.

5. The tri-leaflet prosthetic heart valve according to claim 4 wherein each pivot structure further comprises stop means for arresting movement of the leaflets.

6. The tri-leaflet prosthetic heart valve according to claim 5 wherein the annular body and the leaflets are composed substantially of a non-metallic substance.

7. The tri-leaflet prosthetic heart valve according to claim 6 wherein the non-metallic substance is substantially pyrolitic carbon.

8. The tri-leaflet prosthetic heart valve according to claim 1 further comprising at least three fulcrum means for guiding said leaflets, each of said fulcrum means comprising a post on said inner surface of said annular body between two adjacent pivot structures.

9. The tri-leaflet prosthetic heart valve according to claim 8 wherein each of said leaflets further comprises
   a central planar surface having a curved outer edge for engaging the inner surface of said annular body and an obliquely angled inner edge for engaging adjacent leaflets; and
   two canted substantially planar outer surfaces, each outer surface supporting one of said ears and concave edges, said outer surfaces being deflected from said planar surface towards an upstream side of said valve.

10. The tri-leaflet prosthetic heart valve according to claim 9 wherein each pivot structure further comprises stop means for arresting movement of the leaflets.

11. The tri-leaflet prosthetic heart valve according to claim 10 wherein the annular body and the leaflets are composed substantially of a non-metallic substance.

12. The tri-leaflet prosthetic heart valve according to claim 11 wherein the non-metallic substance is substantially pyrolitic carbon.

* * * * *